United States Patent
Tarmin et al.

(10) Patent No.: US 9,295,458 B2
(45) Date of Patent: Mar. 29, 2016

(54) VASCULAR HOLE CLOSURE DELIVERY DEVICE

(71) Applicants: James S. Tarmin, Media, PA (US); Thanu Anidharan, Downingtown, PA (US)

(72) Inventors: James S. Tarmin, Media, PA (US); Thanu Anidharan, Downingtown, PA (US)

(73) Assignee: Rex Medical, L.P., Conshohocken, PA (US)

(*) Notice: Subject to any disclaimer, the term of this patent is extended or adjusted under 35 U.S.C. 154(b) by 460 days.

(21) Appl. No.: 13/935,881

(22) Filed: Jul. 5, 2013

(65) Prior Publication Data
US 2013/0296926 A1 Nov. 7, 2013

Related U.S. Application Data

(60) Division of application No. 13/274,402, filed on Oct. 17, 2011, now Pat. No. 8,491,629, which is a continuation-in-part of application No. 12/854,988, filed on Aug. 12, 2010, now abandoned, which is a
(Continued)

(51) Int. Cl.
*A61B 17/00* (2006.01)
*A61B 17/04* (2006.01)

(52) U.S. Cl.
CPC ......... *A61B 17/0057* (2013.01); *A61B 17/0467* (2013.01); *A61B 2017/00004* (2013.01); *A61B 2017/00659* (2013.01); *A61B 2017/0409* (2013.01); *A61B 2017/0456* (2013.01); *A61B 2017/0459* (2013.01)

(58) Field of Classification Search
CPC ........... A61B 17/0057; A61B 17/0401; A61B 2017/00575; A61B 2017/00579; A61B 2017/00584; A61B 2017/00588; A61B 2017/00592; A61B 2017/00597; A61B 2017/00601; A61B 2017/00606; A61B 2017/0061; A61B 2017/00615; A61B 2017/00619; A61B 2017/00623; A61B 2017/00628; A61B 2017/00632; A61B 2017/00637; A61B 2017/00641; A61B 2017/0409; A61B 2017/0403; A61B 2017/0404; A61B 2017/0406; A61B 2017/0408; A61B 2017/0411
See application file for complete search history.

(56) References Cited

U.S. PATENT DOCUMENTS

| 2,024,871 A | 12/1935 | Parsons |
| 2,398,220 A | 4/1946 | Gelpcke |
| 2,413,142 A | 12/1946 | Jones et al. |

(Continued)

FOREIGN PATENT DOCUMENTS

| DE | 19604817 | 8/1997 |
| EP | 0637431 | 2/1995 |

(Continued)

*Primary Examiner* — Dianne Dornbusch
(74) *Attorney, Agent, or Firm* — Neil D. Gershon

(57) ABSTRACT

A surgical delivery instrument for delivering a vascular hole closure device having first and second flexible members and a first and second engagement members extending from the respective flexible member. The delivery instrument includes a housing having first and second longitudinally extending openings and first and second projecting surfaces, the first projecting surface extending into the first opening for engagement by the first engagement member and the second projecting surface extending into the second opening for engagement by the second engagement member. The first engagement member is held by the first projecting surface until a predetermined force is applied to the first engagement member during placement of the closure device at a target site.

17 Claims, 8 Drawing Sheets

Related U.S. Application Data continuation-in-part of application No. 12/358,411, filed on Jan. 23, 2009, now Pat. No. 8,070,772.

(60) Provisional application No. 61/409,599, filed on Nov. 3, 2010, provisional application No. 61/241,555, filed on Sep. 11, 2009, provisional application No. 61/066,072, filed on Feb. 15, 2008.

(56) References Cited

U.S. PATENT DOCUMENTS

| | | | |
|---|---|---|---|
| 3,467,089 | A | 9/1969 | Hasson |
| 3,516,403 | A | 6/1970 | Cournut |
| 3,527,223 | A | 9/1970 | Shein |
| 3,675,648 | A | 7/1972 | Pharriss et al. |
| 3,842,827 | A | 10/1974 | Jacobs |
| 3,874,388 | A | 4/1975 | King et al. |
| 3,913,573 | A | 10/1975 | Gutnick |
| 3,937,217 | A | 2/1976 | Kosonen |
| 3,958,576 | A | 5/1976 | Komiya |
| 3,976,079 | A | 8/1976 | Samuels et al. |
| 4,007,743 | A | 2/1977 | Blake |
| 4,031,569 | A | 6/1977 | Jacob |
| 4,117,838 | A | 10/1978 | Hasson |
| 4,286,497 | A | 9/1981 | Shamah |
| 4,317,445 | A | 3/1982 | Robinson |
| 4,485,816 | A | 12/1984 | Krumme |
| 4,505,274 | A | 3/1985 | Speelman |
| 4,512,338 | A | 4/1985 | Balko et al. |
| 4,532,926 | A | 8/1985 | O'Holla |
| 4,610,671 | A | 9/1986 | Luther |
| 4,615,514 | A | 10/1986 | Hamlin |
| 4,638,803 | A | 1/1987 | Rand |
| 4,665,906 | A | 5/1987 | Jervis |
| 4,676,245 | A | 6/1987 | Fukuda |
| 4,705,040 | A | 11/1987 | Mueller et al. |
| 4,744,364 | A | 5/1988 | Kensey |
| 4,796,612 | A | 1/1989 | Reese |
| 4,836,204 | A | 6/1989 | Landymore et al. |
| 4,890,612 | A | 1/1990 | Kensey |
| 4,917,089 | A | 4/1990 | Sideris |
| 4,924,866 | A | 5/1990 | Yoon |
| 4,971,068 | A | 11/1990 | Sahi |
| 5,009,663 | A | 4/1991 | Broome |
| 5,021,059 | A | 6/1991 | Kensey et al. |
| 5,047,047 | A | 9/1991 | Yoon |
| 5,061,274 | A | 10/1991 | Kensey |
| 5,108,420 | A | 4/1992 | Marks |
| 5,108,421 | A | 4/1992 | Fowler |
| 5,123,913 | A | 6/1992 | Wilk et al. |
| 5,123,914 | A | 6/1992 | Cope |
| 5,171,252 | A | 12/1992 | Friedland |
| 5,171,259 | A * | 12/1992 | Inoue ............... A61B 17/0057 606/213 |
| 5,192,300 | A | 3/1993 | Fowler |
| 5,192,301 | A | 3/1993 | Kamiya et al. |
| 5,192,302 | A | 3/1993 | Kensey et al. |
| 5,219,359 | A | 6/1993 | McQuilkin et al. |
| 5,222,974 | A | 6/1993 | Kensey et al. |
| 5,246,441 | A | 9/1993 | Ross et al. |
| 5,269,809 | A | 12/1993 | Hayhurst et al. |
| 5,279,572 | A | 1/1994 | Hokama |
| 5,282,827 | A | 2/1994 | Kensey et al. |
| 5,292,332 | A | 3/1994 | Lee |
| 5,306,254 | A | 4/1994 | Nash et al. |
| 5,312,435 | A | 5/1994 | Nash et al. |
| 5,318,040 | A | 6/1994 | Kensey et al. |
| 5,334,210 | A | 8/1994 | Gianturco |
| 5,350,399 | A | 9/1994 | Erlebacher et al. |
| 5,350,400 | A | 9/1994 | Esposito et al. |
| 5,370,661 | A | 12/1994 | Branch |
| 5,372,146 | A | 12/1994 | Branch |
| 5,385,554 | A | 1/1995 | Brimhall |
| RE34,866 | E | 2/1995 | Kensey et al. |
| 5,391,183 | A | 2/1995 | Janzen et al. |
| 5,409,444 | A | 4/1995 | Kensey et al. |
| 5,411,520 | A | 5/1995 | Nash et al. |
| 5,433,727 | A | 7/1995 | Sideris |
| 5,441,517 | A | 8/1995 | Kensey et al. |
| 5,443,481 | A | 8/1995 | Lee |
| 5,451,235 | A | 9/1995 | Lock et al. |
| 5,474,557 | A | 12/1995 | Mai |
| 5,478,352 | A | 12/1995 | Fowler |
| 5,478,353 | A | 12/1995 | Yoon |
| 5,486,195 | A | 1/1996 | Myers et al. |
| 5,507,754 | A | 4/1996 | Green et al. |
| 5,520,691 | A | 5/1996 | Branch |
| 5,531,759 | A | 7/1996 | Kensey et al. |
| 5,540,716 | A | 7/1996 | Hlavacek |
| 5,545,178 | A | 8/1996 | Kensey et al. |
| 5,549,617 | A | 8/1996 | Green et al. |
| 5,549,633 | A | 8/1996 | Evans et al. |
| 5,591,204 | A | 1/1997 | Janzen et al. |
| 5,593,422 | A | 1/1997 | Muijs Van de Moer et al. |
| 5,620,461 | A | 4/1997 | Muijs Van De Moer et al. |
| 5,630,833 | A | 5/1997 | Katsaros et al. |
| 5,634,936 | A | 6/1997 | Linden et al. |
| 5,643,317 | A | 7/1997 | Pavcnik et al. |
| 5,649,959 | A | 7/1997 | Hannam et al. |
| 5,658,313 | A | 8/1997 | Thal |
| 5,662,681 | A | 9/1997 | Nash et al. |
| 5,674,231 | A | 10/1997 | Green et al. |
| 5,676,689 | A | 10/1997 | Kensey et al. |
| 5,690,674 | A * | 11/1997 | Diaz ............... A61B 17/0057 604/285 |
| 5,700,277 | A | 12/1997 | Nash et al. |
| 5,702,421 | A | 12/1997 | Schneidt |
| 5,707,393 | A | 1/1998 | Kensey et al. |
| 5,709,707 | A | 1/1998 | Lock et al. |
| 5,725,498 | A | 3/1998 | Janzen et al. |
| 5,728,132 | A | 3/1998 | Van Tassel et al. |
| 5,728,133 | A | 3/1998 | Kontos |
| 5,735,875 | A | 4/1998 | Bonutti et al. |
| 5,741,223 | A | 4/1998 | Janzen et al. |
| 5,741,297 | A | 4/1998 | Simon |
| 5,766,206 | A | 6/1998 | Wijkamp et al. |
| 5,769,894 | A | 6/1998 | Ferragamo |
| 5,782,600 | A | 7/1998 | Walsh |
| 5,782,860 | A | 7/1998 | Epstein et al. |
| 5,782,861 | A | 7/1998 | Cragg et al. |
| 5,810,845 | A | 9/1998 | Yoon |
| 5,810,846 | A | 9/1998 | Virnich et al. |
| 5,810,884 | A | 9/1998 | Kim |
| 5,814,056 | A | 9/1998 | Prosst et al. |
| 5,820,628 | A | 10/1998 | Middleman et al. |
| 5,861,003 | A | 1/1999 | Latson et al. |
| 5,893,856 | A | 4/1999 | Jacob et al. |
| 5,910,155 | A | 6/1999 | Ratcliff et al. |
| 5,916,235 | A | 6/1999 | Guglielmi |
| 5,916,236 | A | 6/1999 | Muijs Van de Moer et al. |
| 5,919,207 | A | 7/1999 | Taheri |
| 5,928,266 | A | 7/1999 | Kontos |
| 5,964,782 | A | 10/1999 | Lafontaine et al. |
| 5,976,159 | A | 11/1999 | Bolduc et al. |
| 5,976,174 | A | 11/1999 | Ruiz |
| 5,984,933 | A | 11/1999 | Yoon |
| 5,984,949 | A | 11/1999 | Levin |
| 5,989,268 | A | 11/1999 | Pugsley, Jr. et al. |
| 6,001,110 | A | 12/1999 | Adams |
| 6,007,563 | A | 12/1999 | Nash et al. |
| 6,010,517 | A | 1/2000 | Baccaro |
| 6,015,417 | A | 1/2000 | Reynolds, Jr. |
| 6,024,756 | A | 2/2000 | Huebsch et al. |
| 6,033,427 | A | 3/2000 | Lee |
| 6,045,551 | A | 4/2000 | Bonutti |
| 6,048,357 | A | 4/2000 | Kontos |
| 6,048,358 | A | 4/2000 | Barak |
| 6,056,768 | A | 5/2000 | Cates et al. |
| 6,063,085 | A | 5/2000 | Tay et al. |
| 6,063,106 | A | 5/2000 | Gibson |
| 6,066,160 | A | 5/2000 | Colvin |
| 6,071,300 | A | 6/2000 | Brenneman et al. |
| 6,077,281 | A | 6/2000 | Das |
| 6,077,291 | A | 6/2000 | Das |

(56) References Cited

U.S. PATENT DOCUMENTS

| | | | |
|---|---|---|---|
| 6,080,182 A | 6/2000 | Shaw et al. |
| 6,080,183 A | 6/2000 | Tsugita et al. |
| 6,110,207 A | 8/2000 | Eichhorn et al. |
| 6,113,611 A | 9/2000 | Allen et al. |
| 6,117,159 A | 9/2000 | Huebsch et al. |
| 6,117,161 A | 9/2000 | Li et al. |
| 6,120,524 A | 9/2000 | Taheri |
| 6,126,675 A | 10/2000 | Shchervinsky et al. |
| 6,136,010 A | 10/2000 | Modesitt et al. |
| 6,139,564 A | 10/2000 | Teoh |
| 6,152,948 A | 11/2000 | Addis |
| 6,162,240 A | 12/2000 | Cates et al. |
| 6,171,320 B1 | 1/2001 | Monassevitch |
| 6,171,329 B1 | 1/2001 | Shaw et al. |
| 6,174,322 B1 | 1/2001 | Schneidt |
| 6,179,863 B1 | 1/2001 | Kensey et al. |
| 6,197,042 B1 | 3/2001 | Ginn et al. |
| 6,206,893 B1 | 3/2001 | Klein et al. |
| 6,206,907 B1 | 3/2001 | Marino et al. |
| 6,228,096 B1 | 5/2001 | Marchand |
| 6,231,561 B1 | 5/2001 | Frazier et al. |
| 6,231,592 B1 | 5/2001 | Bonutti et al. |
| 6,251,122 B1 | 6/2001 | Tsukernik |
| 6,261,309 B1 | 7/2001 | Urbanski |
| 6,264,673 B1 | 7/2001 | Egnelöv |
| 6,270,515 B1 | 8/2001 | Linden et al. |
| 6,277,140 B2 | 8/2001 | Ginn et al. |
| 6,290,674 B1 | 9/2001 | Roue et al. |
| 6,293,961 B2 | 9/2001 | Schwartz et al. |
| 6,312,446 B1 * | 11/2001 | Huebsch ............ A61B 17/0057 606/157 |
| 6,328,727 B1 | 12/2001 | Frazier et al. |
| 6,334,865 B1 | 1/2002 | Redmond et al. |
| 6,336,914 B1 | 1/2002 | Gillespie, III |
| 6,342,064 B1 | 1/2002 | Koike et al. |
| 6,346,117 B1 | 2/2002 | Greenhalgh |
| 6,348,053 B1 | 2/2002 | Cachia |
| 6,350,270 B1 | 2/2002 | Roue |
| 6,350,274 B1 | 2/2002 | Li |
| 6,355,052 B1 | 3/2002 | Neuss et al. |
| 6,368,341 B1 | 4/2002 | Abrahamson |
| 6,368,343 B1 | 4/2002 | Bonutti et al. |
| 6,391,037 B1 | 5/2002 | Greenhalgh |
| 6,391,048 B1 | 5/2002 | Ginn et al. |
| 6,409,739 B1 | 6/2002 | Nobles et al. |
| 6,414,664 B1 | 7/2002 | Conover et al. |
| 6,419,669 B1 | 7/2002 | Frazier et al. |
| 6,425,911 B1 | 7/2002 | Akerfeldt et al. |
| 6,436,088 B2 | 8/2002 | Frazier et al. |
| 6,440,152 B1 | 8/2002 | Gainor et al. |
| 6,447,042 B1 | 9/2002 | Jin |
| 6,447,524 B1 | 9/2002 | Knodel et al. |
| 6,451,030 B2 | 9/2002 | Li et al. |
| 6,468,293 B2 | 10/2002 | Bonutti et al. |
| 6,482,179 B1 | 11/2002 | Chu et al. |
| 6,491,714 B1 | 12/2002 | Bennett |
| 6,500,184 B1 | 12/2002 | Chan et al. |
| 6,503,266 B1 | 1/2003 | Sjögren |
| 6,508,828 B1 | 1/2003 | Akerfeldt et al. |
| 6,537,299 B1 | 3/2003 | Hogendijk et al. |
| 6,547,806 B1 | 4/2003 | Ding |
| 6,569,185 B2 | 5/2003 | Ungs |
| 6,569,187 B1 | 5/2003 | Bonutti et al. |
| 6,585,748 B1 | 7/2003 | Jeffree |
| 6,585,750 B2 | 7/2003 | Bonutti et al. |
| 6,596,012 B2 | 7/2003 | Akerfeldt et al. |
| 6,626,937 B1 | 9/2003 | Cox |
| 6,635,073 B2 | 10/2003 | Bonutti |
| 6,648,903 B1 | 11/2003 | Pierson, III |
| 6,663,653 B2 | 12/2003 | Akerfeldt |
| 6,663,655 B2 | 12/2003 | Ginn |
| 6,676,685 B2 | 1/2004 | Pedros et al. |
| 6,682,489 B2 | 1/2004 | Tenerz et al. |
| 6,699,263 B2 | 3/2004 | Cope |
| 6,712,836 B1 | 3/2004 | Berg et al. |
| 6,712,837 B2 | 3/2004 | Akerfeldt et al. |
| 6,749,621 B2 | 6/2004 | Pantages et al. |
| 6,749,622 B2 | 6/2004 | McGuckin, Jr. et al. |
| 6,764,500 B1 | 7/2004 | Muijs van der Moer et al. |
| 6,766,186 B1 | 7/2004 | Hoyns et al. |
| 6,786,915 B2 | 9/2004 | Akerfeldt et al. |
| 6,790,220 B2 | 9/2004 | Morris |
| 6,846,316 B2 | 1/2005 | Abrams |
| 6,855,153 B2 | 2/2005 | Saadat |
| 6,860,895 B1 | 3/2005 | Akerfeldt et al. |
| 6,863,680 B2 | 3/2005 | Ashby |
| 6,909,130 B2 | 6/2005 | Yoda et al. |
| 6,929,655 B2 | 8/2005 | Egnelov |
| 6,932,835 B2 | 8/2005 | Bonutti et al. |
| 6,939,363 B2 | 9/2005 | Akerfeldt |
| 6,949,107 B2 | 9/2005 | McGuckin, Jr. et al. |
| 6,960,224 B2 | 11/2005 | Marino et al. |
| 6,972,027 B2 | 12/2005 | Fallin et al. |
| 6,984,219 B2 | 1/2006 | Ashby |
| 6,997,940 B2 | 2/2006 | Bonutti |
| 7,008,440 B2 | 3/2006 | Sing et al. |
| 7,008,442 B2 | 3/2006 | Brightbill |
| 7,025,756 B2 | 4/2006 | Frazier et al. |
| 7,025,776 B1 | 4/2006 | Houser et al. |
| 7,033,380 B2 | 4/2006 | Schwartz et al. |
| 7,033,393 B2 | 4/2006 | Gainor et al. |
| 7,048,748 B1 | 5/2006 | Ustuner |
| 7,048,755 B2 | 5/2006 | Bonutti et al. |
| 7,083,635 B2 | 8/2006 | Ginn |
| 7,087,073 B2 | 8/2006 | Bonutti |
| 7,094,209 B2 | 8/2006 | Egnelöv |
| 7,115,110 B2 | 10/2006 | Frazier et al. |
| 7,135,032 B2 | 11/2006 | Akerfeldt |
| 7,147,652 B2 | 12/2006 | Bonutti et al. |
| 7,150,757 B2 | 12/2006 | Fallin et al. |
| 7,153,323 B1 | 12/2006 | Teoh et al. |
| 7,169,168 B2 | 1/2007 | Muijs Van de Moer et al. |
| 7,175,648 B2 | 2/2007 | Nakao |
| 7,235,091 B2 | 6/2007 | Thornes |
| 7,267,679 B2 | 9/2007 | McGuckin, Jr. et al. |
| 7,285,097 B2 | 10/2007 | Tenerz |
| 7,288,105 B2 | 10/2007 | Oman et al. |
| 7,316,706 B2 | 1/2008 | Bloom et al. |
| 7,329,270 B2 | 2/2008 | Akerfeldt |
| 7,341,595 B2 | 3/2008 | Hinchliffe et al. |
| 7,361,183 B2 | 4/2008 | Ginn |
| 7,468,068 B2 | 12/2008 | Kolster |
| 7,488,340 B2 | 2/2009 | Kauphusman et al. |
| 7,530,990 B2 | 5/2009 | Perriello et al. |
| 7,566,339 B2 | 7/2009 | Fallin et al. |
| 7,582,105 B2 | 9/2009 | Kolster |
| 7,594,923 B2 | 9/2009 | Fallin et al. |
| 7,597,705 B2 | 10/2009 | Forrsberg et al. |
| 7,618,435 B2 * | 11/2009 | Opolski ............ A61B 17/12022 606/1 |
| 7,618,438 B2 | 11/2009 | White et al. |
| 7,621,937 B2 | 11/2009 | Pipenhagen et al. |
| 7,625,352 B1 | 12/2009 | Ashby et al. |
| 7,637,921 B2 | 12/2009 | Akerfeldt |
| 7,654,963 B2 | 2/2010 | Egnelöv |
| 7,658,751 B2 | 2/2010 | Stone et al. |
| 7,662,160 B2 | 2/2010 | Bojarski et al. |
| 7,662,161 B2 | 2/2010 | Briganti et al. |
| 7,666,199 B2 | 2/2010 | McIntyre |
| 7,717,929 B2 | 5/2010 | Fallman |
| 7,736,378 B2 | 6/2010 | Maahs et al. |
| 7,758,594 B2 | 7/2010 | Lamson et al. |
| 7,775,988 B2 | 8/2010 | Pijls |
| 7,780,699 B2 | 8/2010 | Zhu |
| 7,824,417 B2 | 11/2010 | Magnusson |
| 7,846,180 B2 | 12/2010 | Cerier |
| 7,862,584 B2 | 1/2011 | Lyons |
| 7,931,670 B2 | 4/2011 | Fiehler |
| 7,931,671 B2 | 4/2011 | Tenerz |
| 7,938,846 B2 | 5/2011 | Akerfeldt |
| 7,967,840 B2 | 6/2011 | Chanduszko |
| 8,016,857 B2 | 9/2011 | Sater |
| 8,088,143 B2 | 1/2012 | Akerfeldt |
| 8,105,352 B2 | 1/2012 | Egnelov |

(56) References Cited

U.S. PATENT DOCUMENTS

| | | | |
|---|---|---|---|
| 8,109,968 B2 | 2/2012 | Ashley | |
| 8,118,831 B2 | 2/2012 | Egnelov | |
| 8,118,832 B1 | 2/2012 | Morris | |
| 8,118,833 B2 * | 2/2012 | Seibold | A61B 17/0057 606/215 |
| 8,267,959 B2 | 9/2012 | Fällman | |
| 8,308,762 B2 | 11/2012 | Mahlin | |
| 8,382,793 B2 | 2/2013 | Egnelöv | |
| 8,398,675 B2 | 3/2013 | Egnelöv | |
| 8,444,673 B2 | 5/2013 | Thielen et al. | |
| RE44,297 E | 6/2013 | Akerfeldt | |
| 8,469,944 B2 | 6/2013 | Mahlin | |
| 8,480,686 B2 * | 7/2013 | Bakos | A61B 17/0401 606/139 |
| 8,647,365 B2 | 2/2014 | Tegels | |
| 8,652,166 B2 | 2/2014 | Akerfeldt | |
| 8,663,254 B2 * | 3/2014 | Feussner | A61B 17/0643 606/151 |
| 2001/0010005 A1 * | 7/2001 | Kammerer | A61B 17/064 606/151 |
| 2002/0055767 A1 * | 5/2002 | Forde | A61B 17/0057 623/1.11 |
| 2002/0082622 A1 | 6/2002 | Kane | |
| 2002/0095179 A1 | 7/2002 | Tenerz et al. | |
| 2002/0165561 A1 | 11/2002 | Ainsworth et al. | |
| 2002/0165572 A1 | 11/2002 | Saadat | |
| 2002/0198563 A1 | 12/2002 | Gainor et al. | |
| 2003/0009180 A1 * | 1/2003 | Hinchliffe | A61B 17/0057 606/144 |
| 2003/0050665 A1 | 3/2003 | Ginn | |
| 2003/0055451 A1 | 3/2003 | Jones et al. | |
| 2003/0088256 A1 | 5/2003 | Conston et al. | |
| 2003/0088269 A1 | 5/2003 | Ashby | |
| 2003/0105487 A1 | 6/2003 | Benz et al. | |
| 2003/0130694 A1 | 7/2003 | Bojarski et al. | |
| 2003/0144695 A1 | 7/2003 | McGuckin, Jr. et al. | |
| 2003/0187473 A1 | 10/2003 | Berenstein et al. | |
| 2003/0191495 A1 | 10/2003 | Ryan et al. | |
| 2004/0002764 A1 | 1/2004 | Gainor et al. | |
| 2004/0010287 A1 | 1/2004 | Bonutti | |
| 2004/0039413 A1 | 2/2004 | Akerfeldt | |
| 2004/0049207 A1 * | 3/2004 | Goldfarb | A61B 17/0401 606/139 |
| 2004/0093025 A1 | 5/2004 | Egnelov | |
| 2004/0133236 A1 | 7/2004 | Chanduszko | |
| 2004/0133238 A1 | 7/2004 | Cerier | |
| 2004/0143294 A1 | 7/2004 | Corcoran et al. | |
| 2004/0153103 A1 | 8/2004 | Schwartz et al. | |
| 2004/0158287 A1 | 8/2004 | Cragg et al. | |
| 2004/0176800 A1 | 9/2004 | Paraschac et al. | |
| 2004/0230223 A1 | 11/2004 | Bonutti et al. | |
| 2005/0033326 A1 * | 2/2005 | Briganti | A61B 17/0057 606/151 |
| 2005/0059982 A1 | 3/2005 | Zung et al. | |
| 2005/0065547 A1 | 3/2005 | Marino et al. | |
| 2005/0070957 A1 | 3/2005 | Das | |
| 2005/0075654 A1 | 4/2005 | Kelleher | |
| 2005/0085852 A1 | 4/2005 | Ditter | |
| 2005/0085855 A1 | 4/2005 | Forsberg | |
| 2005/0090859 A1 | 4/2005 | Ravlkumar | |
| 2005/0096696 A1 | 5/2005 | Forsberg | |
| 2005/0096697 A1 | 5/2005 | Forsberg et al. | |
| 2005/0107807 A1 | 5/2005 | Nakao | |
| 2005/0125030 A1 | 6/2005 | Forsberg et al. | |
| 2005/0125031 A1 | 6/2005 | Pipenhagen et al. | |
| 2005/0125032 A1 | 6/2005 | Whisenant et al. | |
| 2005/0169974 A1 | 8/2005 | Tenerz et al. | |
| 2005/0177182 A1 * | 8/2005 | van der Burg | A61B 17/0057 606/157 |
| 2005/0192627 A1 | 9/2005 | Whisenant et al. | |
| 2005/0192630 A1 | 9/2005 | Maas et al. | |
| 2005/0216059 A1 | 9/2005 | Bonutti | |
| 2005/0267524 A1 | 12/2005 | Chanduszko | |
| 2005/0283193 A1 | 12/2005 | Tullberg et al. | |
| 2005/0288786 A1 * | 12/2005 | Chanduszko | A61B 17/0057 623/11.11 |
| 2006/0069408 A1 | 3/2006 | Kato | |
| 2006/0100665 A1 | 5/2006 | Von Oepen et al. | |
| 2006/0106418 A1 | 5/2006 | Seibold et al. | |
| 2006/0135991 A1 * | 6/2006 | Kawaura | A61B 17/0057 606/213 |
| 2006/0142797 A1 | 6/2006 | Egnelov | |
| 2006/0155327 A1 | 7/2006 | Briganti | |
| 2006/0167495 A1 | 7/2006 | Bonutti et al. | |
| 2006/0173492 A1 | 8/2006 | Akerfeldt et al. | |
| 2006/0212073 A1 | 9/2006 | Bonutti et al. | |
| 2006/0217760 A1 | 9/2006 | Widomski et al. | |
| 2006/0217765 A1 | 9/2006 | Bonutti et al. | |
| 2006/0241695 A1 | 10/2006 | Bonutti et al. | |
| 2006/0265009 A1 | 11/2006 | Bonutti | |
| 2006/0271105 A1 | 11/2006 | Foerster et al. | |
| 2006/0276871 A1 | 12/2006 | Lamson et al. | |
| 2007/0010851 A1 | 1/2007 | Chanduszko et al. | |
| 2007/0010857 A1 | 1/2007 | Sugimoto et al. | |
| 2007/0060858 A1 | 3/2007 | Sogard et al. | |
| 2007/0073322 A1 | 3/2007 | Mikkaichi et al. | |
| 2007/0073337 A1 * | 3/2007 | Abbott | A61B 17/0057 606/213 |
| 2007/0073345 A1 | 3/2007 | Pipenhagen et al. | |
| 2007/0088388 A1 * | 4/2007 | Opolski | A61B 17/0057 606/213 |
| 2007/0135826 A1 * | 6/2007 | Zaver | A61B 17/0057 606/157 |
| 2007/0149987 A1 | 6/2007 | Wellman et al. | |
| 2007/0149998 A1 | 6/2007 | Wicks et al. | |
| 2007/0149999 A1 | 6/2007 | Szabo et al. | |
| 2007/0150002 A1 | 6/2007 | Szabo et al. | |
| 2007/0156175 A1 | 7/2007 | Weadock et al. | |
| 2007/0185529 A1 * | 8/2007 | Coleman | A61B 17/0057 606/213 |
| 2007/0185532 A1 | 8/2007 | Stone et al. | |
| 2007/0198038 A1 * | 8/2007 | Cohen | A61B 17/0401 606/150 |
| 2007/0239208 A1 | 10/2007 | Crawford | |
| 2007/0239209 A1 | 10/2007 | Fallman | |
| 2007/0244518 A1 | 10/2007 | Callaghan | |
| 2007/0255316 A1 | 11/2007 | McIntyre | |
| 2007/0276437 A1 | 11/2007 | Call | |
| 2008/0071310 A1 | 3/2008 | Hoffman et al. | |
| 2008/0082128 A1 | 4/2008 | Stone | |
| 2008/0114395 A1 | 5/2008 | Mathisen et al. | |
| 2008/0140092 A1 | 6/2008 | Stone et al. | |
| 2008/0243182 A1 * | 10/2008 | Bates | A61B 17/0057 606/213 |
| 2009/0030450 A1 | 1/2009 | Preinitz et al. | |
| 2009/0036919 A1 | 2/2009 | Preinitz et al. | |
| 2009/0036920 A1 | 2/2009 | Preinitz et al. | |
| 2009/0043333 A1 * | 2/2009 | Preinitz | A61B 17/0057 606/215 |
| 2009/0076541 A1 * | 3/2009 | Chin | A61B 17/0057 606/215 |
| 2009/0088778 A1 * | 4/2009 | Miyamoto | A61B 17/0401 606/144 |
| 2009/0163934 A1 * | 6/2009 | Raschdorf, Jr. | A61B 17/00234 606/139 |
| 2009/0177225 A1 | 7/2009 | Nunez et al. | |
| 2009/0210004 A1 | 8/2009 | McGuckin, Jr. et al. | |
| 2009/0216267 A1 | 8/2009 | Willard et al. | |
| 2009/0234377 A1 | 9/2009 | Mahlin et al. | |
| 2009/0248064 A1 | 10/2009 | Preinitz | |
| 2009/0326460 A1 | 12/2009 | Beardsley | |
| 2010/0114156 A1 * | 5/2010 | Mehl | A61B 17/0057 606/213 |
| 2010/0312224 A1 | 12/2010 | Atthoff et al. | |
| 2011/0071551 A1 * | 3/2011 | Singhatat | A61B 17/0401 606/145 |
| 2011/0082495 A1 * | 4/2011 | Ruiz | A61B 17/0057 606/213 |

(56) References Cited

U.S. PATENT DOCUMENTS

| | | |
|---|---|---|
| 2011/0270307 A1 | 11/2011 | Szabo |
| 2012/0078294 A1 | 3/2012 | Tarmin et al. |

FOREIGN PATENT DOCUMENTS

| | | |
|---|---|---|
| EP | 0920842 | 6/1999 |
| EP | 1671591 | 6/2006 |
| EP | 1671592 | 6/2006 |
| EP | 2055236 | 5/2009 |
| EP | 2294986 | 3/2011 |
| EP | 2412317 | 2/2012 |
| WO | WO 94/28800 | 12/1994 |
| WO | 9520916 | 8/1995 |
| WO | 95/32670 | 12/1995 |
| WO | 9707741 | 3/1997 |
| WO | 9827868 | 7/1998 |
| WO | 99/00055 | 1/1999 |
| WO | 9905977 | 2/1999 |
| WO | 9938454 | 8/1999 |
| WO | WO 01/40348 | 11/2000 |
| WO | WO 00/78226 | 12/2000 |
| WO | 2004012601 | 2/2004 |
| WO | 2004098418 | 11/2004 |
| WO | 0112864 | 12/2004 |
| WO | 2006093970 | 9/2006 |

\* cited by examiner

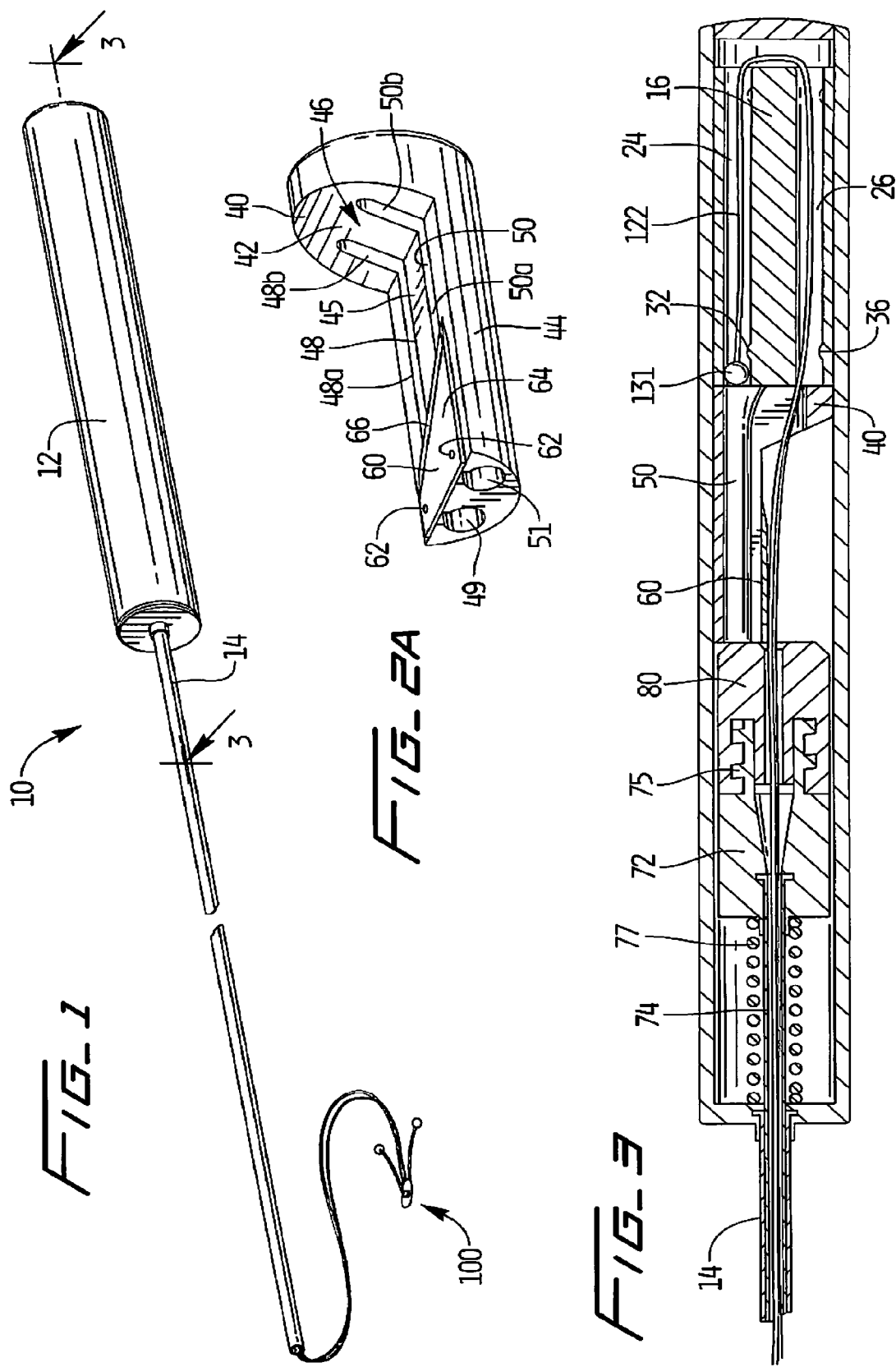

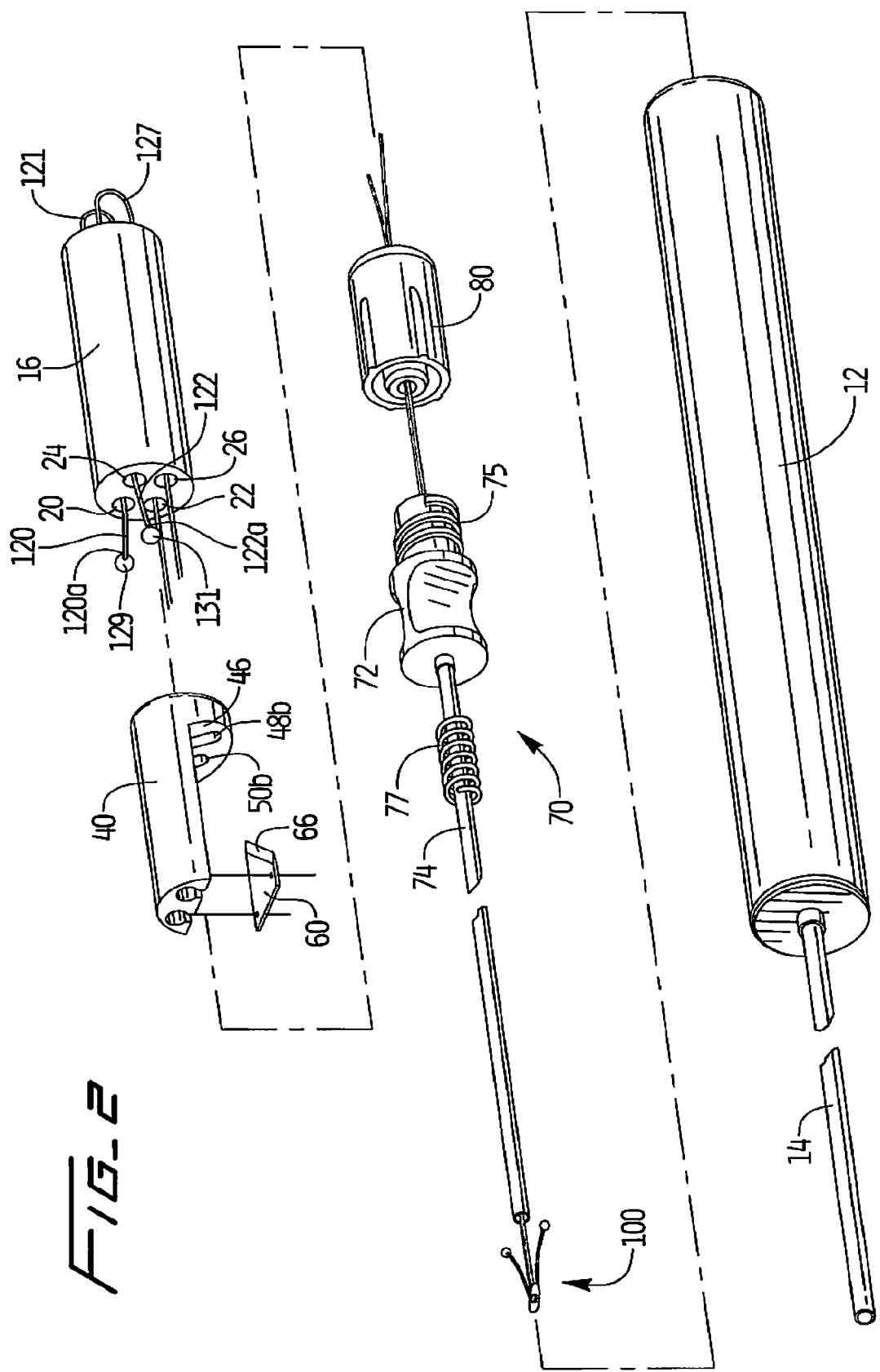

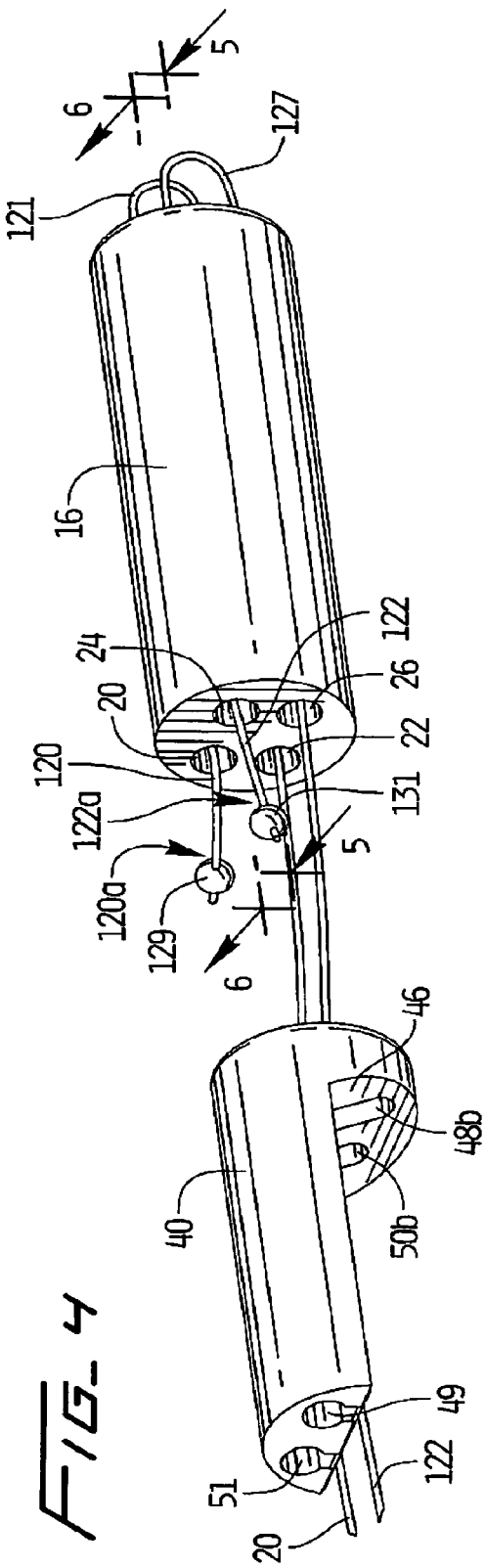
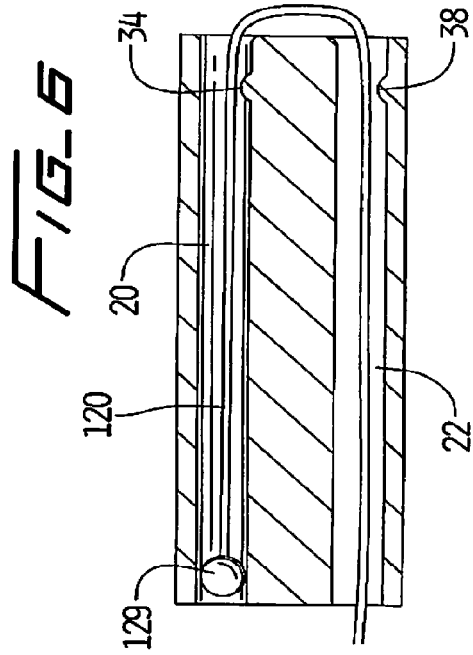
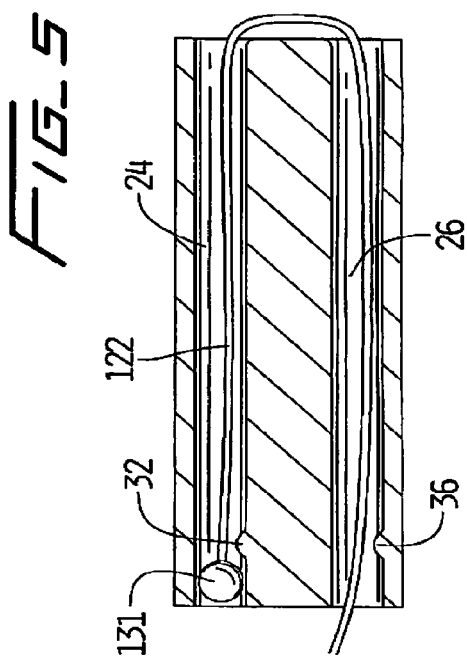

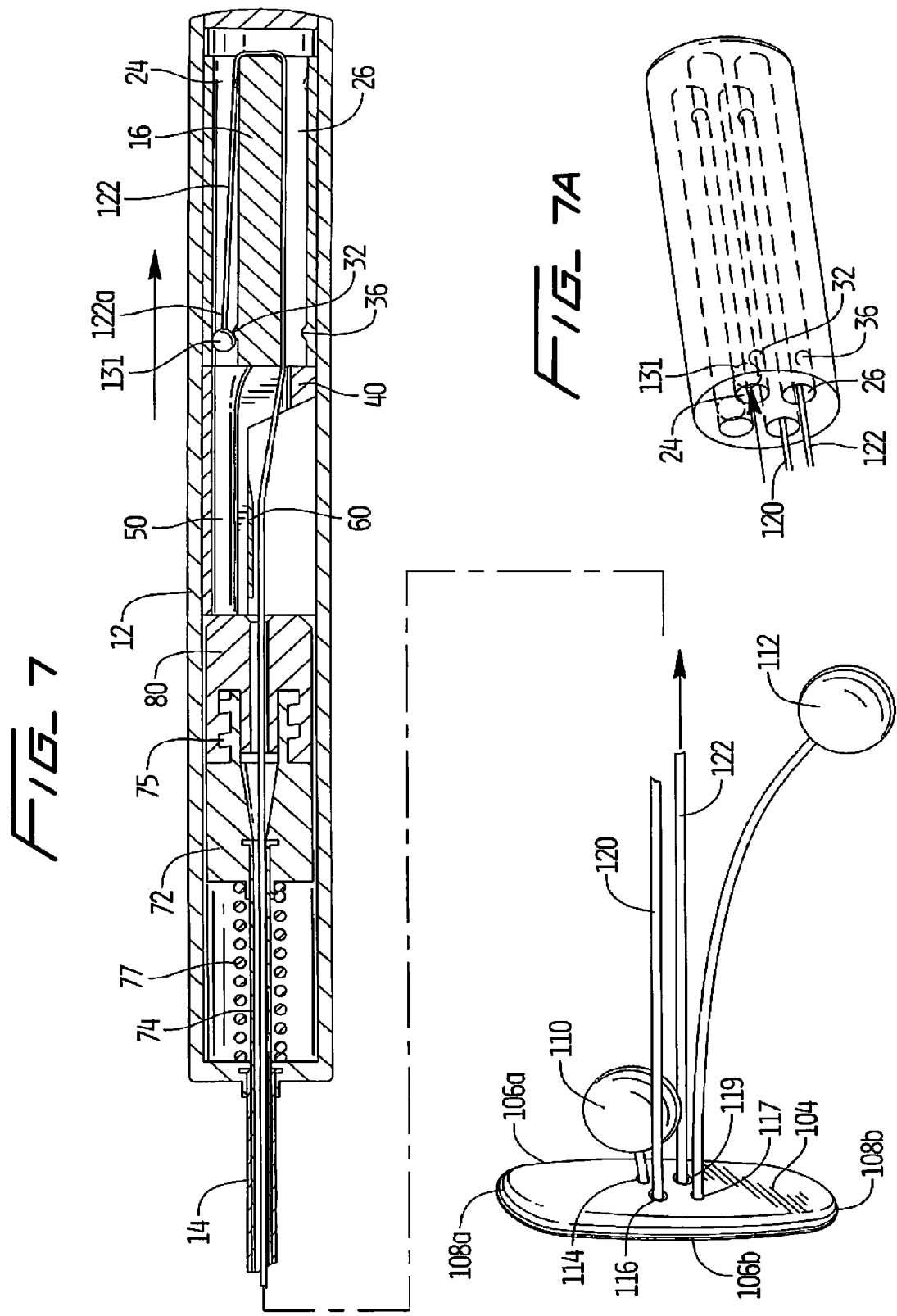

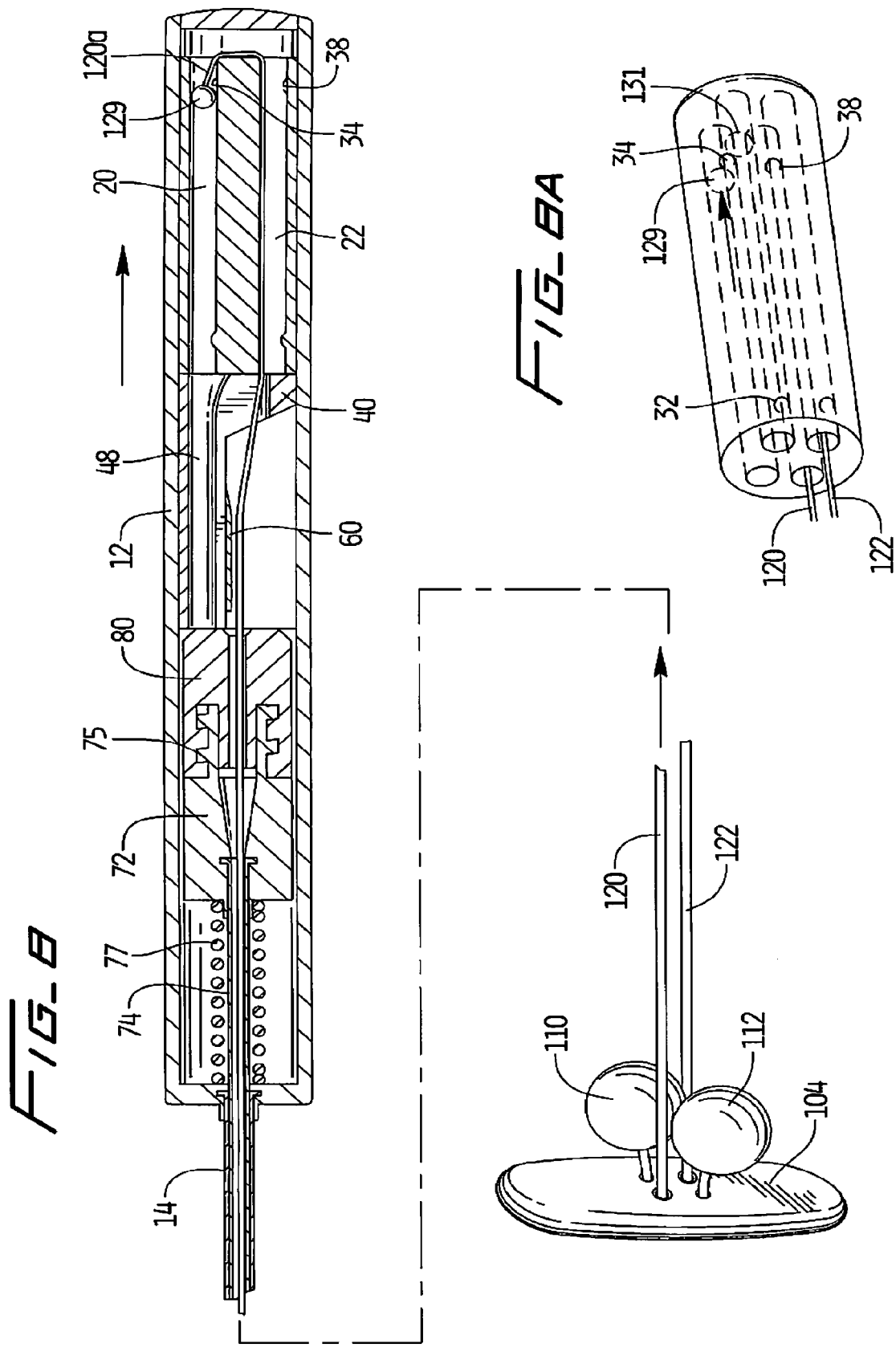

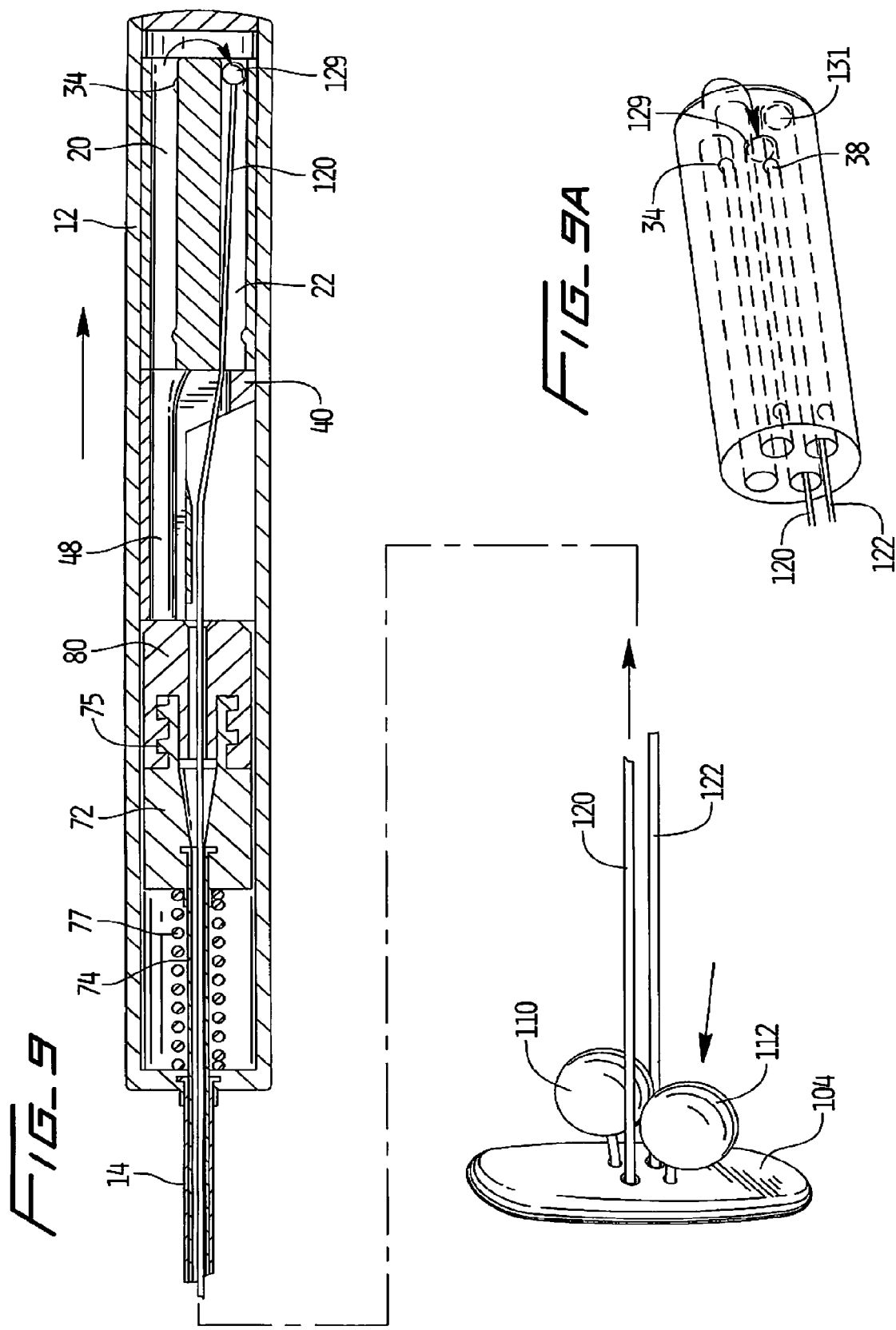

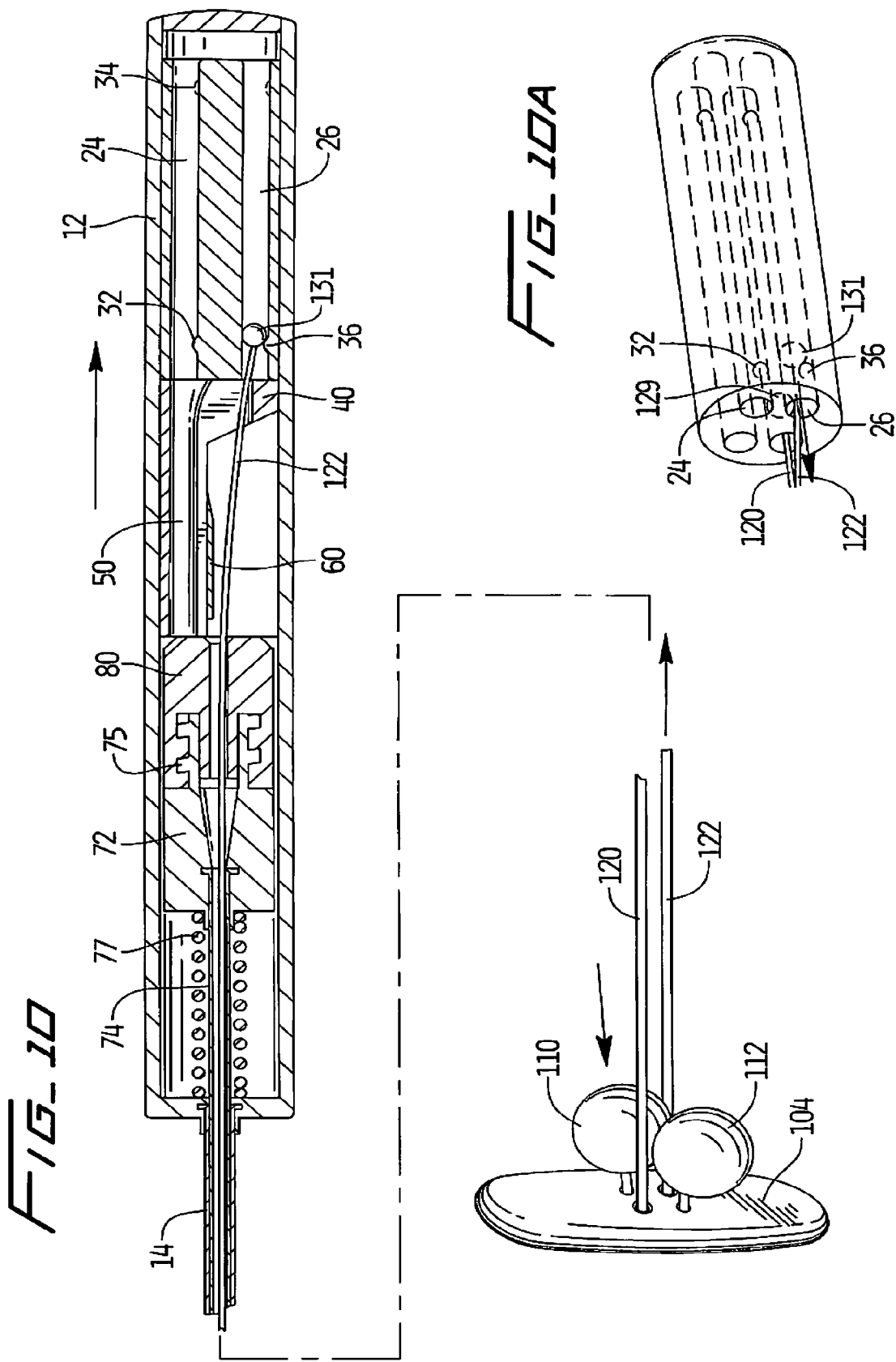

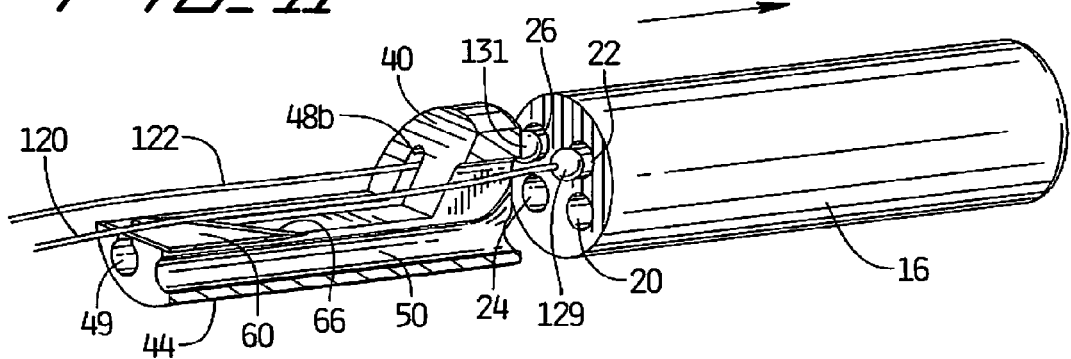
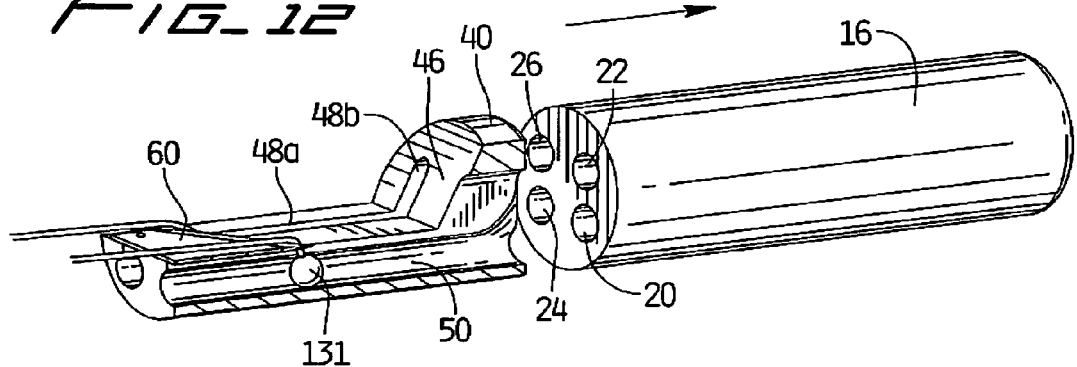
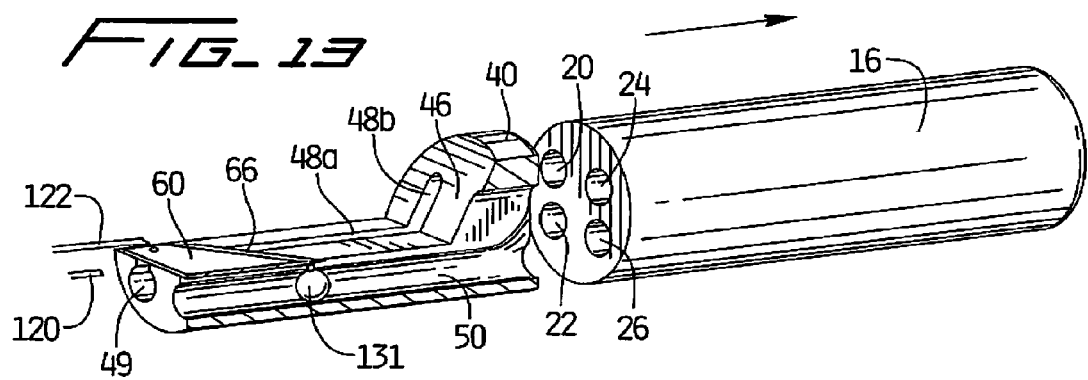

VASCULAR HOLE CLOSURE DELIVERY DEVICE

This application is a division of application Ser. No. 13/274,402, filed Oct. 17, 2011, now U.S. Pat. No. 8,491,629, which claims priority from application Ser. No. 61/409,599, filed Nov. 3, 2010 and is a continuation in part of application Ser. No. 12/854,988, filed Aug. 12, 2010, now abandoned, which claims priority from provisional application No. 61/241,555, filed Sep. 11, 2009 and is a continuation in part of application Ser. No. 12/358,411, filed Jan. 23, 2009, now U.S. Pat. No. 8,070,772, which claims priority from provisional application Ser. No. 61/066,072, filed Feb. 15, 2008. The entire contents of each of these applications are incorporated herein by reference.

BACKGROUND

1. Technical Field

This application relates to a delivery device for a vascular device and more particularly to a delivery device for a vascular hole closure device.

2. Background of Related Art

During certain types of vascular surgery, catheters are inserted through an incision in the skin and underlying tissue to access the femoral artery in the patient's leg. The catheter is then inserted through the access opening made in the wall of the femoral artery and guided through the artery to the desired site to perform surgical procedures such as angioplasty or plaque removal. After the surgical procedure is completed and the catheter is removed from the patient, the access hole must be closed. This is quite difficult not only because of the high blood flow from the artery, but also because there are many layers of tissue that must be penetrated to reach the femoral artery.

Several approaches to date have been used to close femoral access holes. In one approach, manual compression by hand over the puncture site is augmented by a sandbag or weight until the blood coagulates. With this approach, it can take up to six hours for the vessel hole to close and for the patient to be able to ambulate. This inefficiency increases the surgical procedure time as well as the overall cost of the procedure since the hospital staff must physically maintain pressure and the patient's discharge is delayed because of the inability to ambulate.

In another approach to close the vessel puncture site, a clamp is attached to the operating table and the patient's leg. The clamp applies pressure to the vessel opening. The patient, however, must still be monitored to ensure the blood is coagulating, requiring additional time of the hospital staff and increasing the cost of the procedure.

To avoid the foregoing disadvantages of manual pressure approaches, suturing devices have been developed. One such suturing device, sold by Abbott, advances needles adjacent the vessel wall opening and pulls suture material outwardly through the wall adjacent the opening. The surgeon then ties a knot in the suture, closing the opening. One difficulty with the procedure involves the number of steps required by the surgeon to deploy the needles, capture the suture, withdraw the suture, and tie the knot and secure the suture. Moreover, the surgeon cannot easily visualize the suture because of the depth of the femoral artery (relative to the skin) and essentially ties the suture knot blindly or blindly slips a pre-tied knot into position. Additionally, the ability to tie the knot varies among surgeons; therefore success and accuracy of the hole closure can be dependent on the skill of the surgeon. Yet another disadvantage of this suturing instrument is that the vessel opening is widened for insertion of the instrument, thus creating a bigger opening to close in the case of failure to deliver the closure system. It is also difficult to pass the needle through calcified vessels.

U.S. Pat. No. 4,744,364 discloses another approach for sealing a vessel puncture in the form of a device having an expandable closure member with a filament for pulling it against the vessel wall. The closure member is held in place by a strip of tape placed on the skin to hold the filament in place. However, the closure device is still subject to movement which can cause leakage through the puncture. Additionally, if the suture becomes loose, the closure member is not retained and can flow downstream in the vessel. Moreover, since the suture extends through the skin, a potential pathway for infection is created. The closure device in U.S. Pat. No. 5,545,178 includes a resorbable collagen foam plug located within the puncture tract. However, since coagulation typically takes up to twenty minutes and blood can leak in between the plug and tissue tract, manual pressure must be applied to the puncture for a period of time, until the collagen plug expands within the tract.

It would therefore be advantageous to provide a device which would more quickly and effectively close openings (punctures) in vessel walls. Such device would advantageously avoid the aforementioned time and expense of applying manual pressure to the opening, simplify the steps required to close the opening, avoid widening of the opening, and more effectively retain the closure device in the vessel.

Commonly assigned U.S. Pat. No. 7,662,161 discloses effective vascular hole closure devices which have the foregoing advantages. It would be further advantageous to provide a vascular hole closure device which is adjustable to accommodate different tissue thicknesses and applies a more constant clamping/retaining force between the intravascular and extravascular components of the device irrespective of tissue thickness. Such adjustability is achieved in the vascular hole closure devices of copending commonly assigned application Ser. No. 12/854,988, filed Aug. 12, 2010, (hereinafter the '988 application) published as 2011/0029013, the entire contents of which are incorporated herein by reference.

The need exists for an effective delivery device to deliver the closure device of the '988 application to the target site to close the vascular access hole.

SUMMARY

The present invention in one aspect provides a surgical delivery instrument for delivering a vascular hole closure device having a first flexible member and a first engagement member extending therefrom and a second flexible member having a second engagement member extending therefrom. The delivery instrument includes a housing having first and second longitudinally extending openings and first and second projecting surfaces, the first projecting surface extending into the first opening for engagement by the first engagement member and the second projecting surface extending into the second opening for engagement by the second engagement member. The first engagement member is held by the first projecting surface until a predetermined force is applied to the first engagement member during placement of the closure device at a target site.

In a preferred embodiment, the second engagement member is held by the second projecting surface until a predetermined force is applied to the second engagement member during placement of the closure device at the target site.

In preferred embodiments, the first and second flexible members of the closure device are sutures and the delivery instrument further comprises a cutting member positioned within the housing for severing the sutures.

In some embodiments, the delivery instrument further includes a first channel communicating with the first longitudinally extending opening and a second channel communicating with the second longitudinally extending opening, the first and second channels formed in a wall extending at an angle to a longitudinal axis of the first and second longitudinally extending openings.

The delivery instrument can further include a third projecting surface extending into the first longitudinally extending opening and axially spaced from the first projecting surface, and a fourth projecting surface extending into the second longitudinally extending opening and axially spaced from the second projecting surface. In some embodiments, a) the first engagement member is engageable with the first projecting surface when a first force is applied and subsequently engageable with the third projecting surface when a subsequent force is applied and b) the second engagement member is engageable with the second projecting surface when a second force is applied and subsequently engageable with the fourth projecting surface when a subsequent force is applied.

In some embodiments, the flexible members are sutures and the first and second engagement members are positioned on a proximal portion of the respective suture. In some embodiments, the first and second engagement members are substantially spherical in configuration.

In another aspect, the present invention provides in combination a vascular hole closure device and a delivery instrument for delivering the vascular hole closure device. The vascular hole closure device has a covering member at a distal end for positioning internal a vessel, a first retainer for positioning external of the vessel, a first flexible member extending between the covering member and first retainer and a first engagement member at a proximal portion of the flexible member. The delivery instrument includes a housing having a first stop, the first engagement member engageable with the first stop and overriding the first stop when a predetermined proximal force is applied to the delivery instrument.

In some embodiments, the housing of the delivery instrument includes a lumen in which the first engagement member travels during delivery, and the first stop includes an abutment member in the form of a projecting surface extending transversely of the lumen.

In some embodiments, the delivery instrument includes a cutting member to sever the first flexible member upon delivery of the hole closure device to a surgical site.

Preferably, the closure device has a second retainer and a second flexible member extending between the second retainer and covering member. The delivery instrument can include a second stop, the second engagement member engageable with the second stop and overriding the second stop when a predetermined proximal force is applied to the delivery instrument. Preferably, pulling of the first flexible member advances the first retainer toward the covering member and pulling of the second flexible member advances the second retainer toward the covering member.

In preferred embodiments, the covering member, first and second retainers and first and second flexible members are composed of a resorbable material.

In another aspect, the present invention provides a method of delivering a vascular hole closure device, the method comprising:

providing a vascular hole closure device having a covering member, a first retainer, a first flexible member extending between the covering member and first retainer and a first engagement member extending from the first flexible member;

providing a delivery instrument containing the first flexible member;

inserting a distal portion of the delivery instrument into the vessel;

exposing the covering member for placement inside the vessel;

moving the delivery instrument proximally until the first engagement member is forced pass a first stop and comes into contact with a second stop within the delivery instrument to move the first retainer toward the covering member.

In preferred embodiments, the closure device includes a second retainer and a second flexible member extending between the covering member and second retainer, and moving the delivery instrument proximally moves a second engagement member extending from the second flexible member into a contact with a third stop within the delivery instrument to move the second retainer toward the covering member.

In some embodiments, proximal movement of the delivery instrument causes the first flexible member to be severed.

In some embodiments, the covering member is pivotable between a more longitudinal orientation for delivery and a transverse position for placement.

In some embodiments, further proximal movement of the delivery instrument moves the second engagement member past the third stop and into contact with a fourth stop within the delivery instrument.

In some embodiments, proximal movement of the delivery instrument causes the first engagement member to slide within a channel of a channel housing to enable the first flexible member to contact a cutting member positioned within the tubular member to sever the first flexible member. In some embodiments, such proximal movement also severs the second flexible member.

BRIEF DESCRIPTION OF THE DRAWINGS

Preferred embodiment(s) of the present disclosure are described herein with reference to the drawings wherein:

FIG. 1 is a perspective view of a first embodiment of the hole closure delivery instrument of the present invention;

FIG. 2 is a an exploded view of the delivery instrument of FIG. 2;

FIG. 2A is a bottom perspective view of the channel housing;

FIG. 3 is a longitudinal cross-sectional view taken along line 3-3 of FIG. 1;

FIG. 4 is a perspective view illustrating the bump housing and channel housing of the delivery instrument, illustrating the retainers of the closure device in the initial position;

FIG. 5 is a cross-sectional view taken along line 5-5 of FIG. 4 showing the position of the first retainer;

FIG. 6 is a cross-sectional view taken along line 6-6 of FIG. 4 showing the position of the second retainer;

FIG. 7 is a cross-sectional view similar to FIG. 3 illustrating initial proximal movement of the housing of the delivery instrument to advance the first retainer of the closure device toward the covering member;

FIG. 7A is a perspective view illustrating the suture position of FIG. 7;

FIG. 8 is a cross-sectional view corresponding to the cross-section of FIG. 6 to show movement of the second retainer, the Figure illustrating further proximal movement of the housing of the delivery instrument to advance the second retainer of the closure device toward the covering member;

FIG. 8A is a perspective view illustrating the suture position of FIG. 8;

FIG. 9 is a cross-sectional view similar to FIG. 8 illustrating further proximal movement of the housing of the delivery instrument to advance the second retainer of the closure device further toward the covering member;

FIG. 9A is a perspective view illustrating the suture position of FIG. 9;

FIG. 10 is a cross-sectional view similar to FIG. 7 illustrating further proximal movement of the housing of the delivery instrument to advance the first retainer of the closure device further toward the covering member;

FIG. 10A is a perspective view illustrating the suture position of FIG. 10;

FIG. 11 is a perspective view of the bump housing and a partial cut away view of the channel housing illustrating exiting of the suture from the bump housing;

FIG. 12 is a perspective view similar to FIG. 11 illustrating movement of the engagement members along the channel and the sutures coming into contact with the cutting blade; and FIG. 13 is a perspective view of the bump housing and channel housing with the sutures severed.

DETAILED DESCRIPTION OF PREFERRED EMBODIMENTS

Referring now in detail to the drawings where like reference numerals identify similar or like components throughout the several views, the present application is directed to a delivery device for delivering a vascular hole (aperture) closure device of the present invention. The closure device is intended to close an aperture in the vessel wall, typically formed after removal of a catheter previously inserted through the vessel wall into the vessel lumen for performing angioplasty or other interventional procedures. The aperture extends through the patient's skin and underlying tissue, through the external wall of the vessel, through the wall of the vessel, and through the internal wall of the vessel to communicate with the internal lumen of the vessel. The closure device of the present invention has an intravascular component to block blood flow and an extravascular component to retain the intravascular component.

The closure device is illustrated in FIGS. 7-10 in various stages of delivery and is described in more detail in patent application Ser. No. 12/854,988, filed Aug. 12, 2010, the entire contents of which are incorporated herein by reference. The closure device includes a covering member or patch 104 positioned within the vessel against the internal wall of the vessel to block blood flow and two retainers 110, 112 positioned external of the vessel wall to retain the covering member 104 in its blocking position. Each retainer 110, 112 is preferably spherical in configuration (although other configurations are contemplated) and is fixedly attached to a respective suture 122, 120, such that pulling of the respective suture advances the attached retainer toward the covering member 104 to ultimately position the retainers 110, 112 in a side by side relationship either against or adjacent the external surface of the vessel wall.

Covering member 104, preferably elongated in configuration as shown, is retained in a delivery sheath in a longitudinal position for delivery to the vessel, and then pivots to a transverse position within the vessel lumen (substantially perpendicular to an axis extending through the aperture) for orientation to cover (patch) the vessel aperture on the internal side. This movement is illustrated in FIGS. 37A-37D of U.S. Pat. No. 7,662,161, the entire contents of which are incorporated herein by reference (hereinafter the '161 patent).

The elongated covering member 104 functions to cover (patch) the internal opening in the vessel wall to prevent the egress of blood. The covering member 104 is preferably somewhat oval shaped with elongated substantially parallel side walls 106a, 106b, and end walls 108, 108b connecting the side walls 106a, 106b. Other shapes of the covering member are also contemplated. The end walls 106a, 106b can have substantially straight wall portions, or curved wall portions. Covering member preferably has a thicker region in the central region than the first and second end regions. Other dimensions are also contemplated.

The longitudinal axis of covering member 104 defines a lengthwise dimension and transverse axes define a shorter widthwise dimensions. The widthwise dimension of the covering member 104 is preferably, for a 6 Fr device, in the range of about 2.5 mm to about 3.5 mm, and more preferably about 3.1 mm. Other dimensions are also contemplated. The width preferably is at least substantially equal to the dimension of the internal opening in the vessel wall to effectively cover the opening. In a preferred embodiment, the covering member 40 has a length in the range of about 7.5 mm to about 9 mm (in a 6 French system), and preferably about 8 mm.

It should be appreciated that alternatively the covering member could be provided with an enlarged width region as illustrated in the embodiment of FIG. 1 of the '161 patent. The covering member could also be configured asymmetrically so that the enlarged region is off-centered to accommodate widening of the aperture as the member is pulled at an angle. The covering member could also be configured in a paddle shape with a narrowed region adjacent a wider region as in FIGS. 9B-9E of the '161 patent. Other covering member configurations including those disclosed in the '161 patent could be utilized with the retainers of this present application.

The elongated covering member can be composed of materials such as polycarbonate or polyurethane. Preferably it is composed of resorbable materials such as lactide/glycolide copolymers that after a period of time resorb in the body. If composed of resorbable material, the covering member could optionally have regions of varying resorbability. Varying degrees of resorbability can be achieved for example by utilizing different materials having differing resorbable characteristics or by varying the mass of the covering member (increased mass increases resorbtion time).

Spherical retainers 110, 112 are preferably composed of resorbable material. In a preferred embodiment, the diameter of each retainer 110, 112 is about 0.090 inches to about 0.095 inches, although other dimensions are contemplated. Although shown as spheres, other shapes including other rounded shapes are also contemplated. The retainers could alternatively be made of non-absorbable polymeric or metallic material.

When the retainers 110, 112 are released from the delivery instrument, they are spaced further from the covering member 104. They are then configured to be advanced toward the covering member 104. More specifically, each retainer 110, 112 is fixedly secured to a respective flexible connecting member such as suture 120, 122. Sutures 120, 122 are preferably made of polymeric material and are preferably resorbable, composed of a material such as polydioxanome. It is also contemplated that alternatively a metallic material could be utilized. The sutures, retainers and covering member can be made of the same or different resorbable material, and/or have the same or different resorption times.

Details of the hole closure device as well as various embodiments of the device are shown and described in the '988 patent application previously incorporated by reference herein in its entirety.

Suture 120 has a proximal end 120a and an opposite end secured to retainer 112 by molding, gluing, forming a knot, or other methods. Similarly, suture 122 has a proximal end 122a and an opposite end secured to retainer 110 in any of the foregoing manners. Various methods of attachment are shown and described in the '988 application.

To advance the retainers 110, 112 toward the vessel wall (and covering member), the proximal end of each suture 122, 120 is pulled proximally, thereby moving the respective retainer in the opposite direction closer to the aperture and vessel wall. This is described in detail below in conjunction with the delivery instrument. Note that once the retainers 110, 112 are tightened against the tissue, a sufficient retention force is maintained, i.e. a proximal pulling force on the covering member 104 to pull it slightly proximally against the vessel wall. The retainers 110, 112 therefore help to prevent the covering member 104 from separating from the vessel wall (e.g. moving in the direction toward the opposing vessel wall) which could create an unwanted gap between the covering member 104 and the vessel opening to allow blood flow. The extent to which the retainers 110, 112 move toward the wall (and thus their distance from the vessel wall in their final placement position) will depend on the tissue thickness. Thus, the closure device can adjust for different tissue thicknesses and apply a constant retention force regardless of tissue thickness.

The covering member 104 has a first pair of holes and a second pair of holes. The first pair of holes 116, 117 receive suture 120 and the second pair of holes 119, 114 receive suture 122. Holes 114, 117 have a smaller diameter than holes 116, 119. The larger hole 116 is dimensioned to receive suture 120 for free unrestricted movement of the suture 120 therethrough and therefore easier application of spherical retainer 112. Similarly, the larger hole 119 is dimensioned to receive suture 122 for free unrestricted movement of the suture 122 therethrough and therefore for easier application (movement) of spherical retainer 110. Smaller hole 114 is dimensioned to frictionally engage suture 122 so that tension is applied to the suture 122. It is dimensioned so that the suture 122 can be pulled through the hole 114 if sufficient force is applied by pulling on proximal end 122a, but if such predetermined force is not applied, the suture will remain frictionally engaged within the wall of the opening 114 and not move. In this manner, when tension on proximal end 122a is terminated, the suture 122 and thus the spherical retainer 110 will remain in position. Suture 120 operates in a similar manner, with smaller opening 117 dimensioned to frictionally engage and resist movement of the suture 120 to retain spherical retainer 112 in position. Preferably, each hole 114, 117 has an inwardly angled wall transitioning into a reduced diameter region and an outwardly angled wall transitioning back to a larger diameter. The angled walls facilitate movement of the suture when tension is applied, with the reduced diameter region frictionally securing the suture. Hole 117 has a similar configuration as hole 114 and thus also contains similar angled walls. In this manner, when tension on proximal end 120a and on proximal end 122a is terminated, the respective suture 120 and 122 and thus the respective spherical retainer 112 and 110 will remain in position.

A crimp or a bead can be attached to the suture, or a knot formed in the suture, creating a diameter larger than the diameter of portion within the retainer which forms a shoulder to block movement of the respective spherical retainer 110 or 112. Consequently, this frictional engagement prevents the respective retainer from sliding in the direction away from the covering member 104 while the shoulder prevents the retainer from sliding in the direction toward the covering member 104. The retainer 112 and suture 120 preferably have the same structure and engagement/retention as retainer 110 and suture 122.

Note that during delivery the covering member 104 emerges from the delivery sheath and moves from a tilted position, more aligned or in preferred embodiments substantially aligned with the longitudinal axis of the sheath, to a transverse position within the vessel substantially perpendicular to the longitudinal axis of the sheath.

As can be appreciated, after delivery of the covering member 104 inside the vessel, covering member 104 is pulled proximally to abut the internal opening on the internal side of the vessel to cover (patch) the opening and the sutures extend through the opening in the vessel wall. Note that in the delivery position, the retainers 110 and 112 are preferably in a stacked relationship within the delivery instrument to minimize the transverse dimension of the delivery system.

Then, to retain the covering member 104 in position against the vessel wall to block blood flow therethrough, sutures 120, 122 are pulled proximally from their proximal ends 120a, 122a, thereby advancing the retainers 112, 110 toward the vessel wall and covering member 104. The retainers 112, 110 can be moved to a position contiguous to the vessel wall, or depending on tissue thickness, may be adjacent the wall with some tissue interposed between the retainers and vessel wall. The retainers 110, 112 in this position apply a proximal force on the elongated covering member 104 to limit movement of the covering member 104 into the vessel. The retainers in this placement position are preferably in a substantially side by side relationship. The instrument of the present invention for delivering these elements to the target site to close the vessel opening is described in detail below.

As shown in FIG. 10, in the side by side relationship, the retainers 110, 112 are alongside in a transverse orientation with respect to covering member 104. That is, they are positioned along the width of the covering member 104. However, it is also contemplated that the retainers in the placement position can be in a lengthwise orientation (substantially parallel to the longitudinal axis of the covering member). The retainers could also be in other side by side arrangements at angles to the longitudinal axis. Alternatively, the retainers can be partially stacked in the placement position.

Turning now to the delivery instrument of the present invention and with initial reference to FIGS. 1, 2 and 4, the delivery instrument is designated generally by reference numeral 10 and includes a handle or housing 12 and an elongated tube 14 extending distally from the handle 12. Closure device 100 is shown outside the delivery instrument 10 in FIGS. 1 and 2.

The delivery instrument for inserting the closure device extends through an opening in the patient's skin, through the underlying tissue, through an external opening in the vessel wall, through the aperture in the vessel wall, and through an internal opening on the internal side of the vessel wall into the vessel lumen.

Elongated tube 14 can include a flared distal end to facilitate delivery of the closure device.

The handle housing 12 includes a bump housing 16 with longitudinally extending substantially parallel openings or lumens 20, 22, 24 and 26. Openings 20 and 22 receive suture 120 and openings 24 and 26 receive suture 122 of closure device 100. As shown in FIG. 4, suture 120 loops at loop 121 from opening 20 into opening 22 and suture 122 loops at loop 127 from opening 24 to opening 26.

Contained within the bump housing 28 are a series of stops in the form of projecting members or abutment members which provide resistance to movement of the sutures 120, 122. In the illustrated embodiment, the abutment/projecting members are each in the form of a bump extending transversely into the longitudinally extending opening. This resistance is achieved by the provision of an engagement member at the proximal portion of suture 120 and suture 122.

More specifically, an engagement member 129, illustratively substantially spherical in configuration, although other shapes are contemplated, is positioned at the proximal end 120a of suture 120. Similarly, an engagement member 131, illustratively substantially spherical in configuration, although other shapes are contemplated, is positioned at the proximal end 122a of suture 122. Engagement members 129, 131 can be attached by methods such as crimping, tying a knot, overmolding, etc. and are configured to engage bumps on the bump housing 16 to provide resistance to suture movement. As noted above, openings 20, 22, 24 and 26 preferably extend longitudinally along the length of the bump housing 16, i.e. from the proximal to the distal end.

A first set of bumps 32, 36 extend into longitudinal openings 24, 26, respectively, (see e.g. FIGS. 3 and 5) and a second set of bumps 34, 38 extend into longitudinal openings 20, 22, respectively (see e.g. FIGS. 6 and 8) which form stops as described below.

With reference to FIGS. 2, 2A and 4, a channel housing 40 has a proximal region 42 and a region 44, which is illustratively substantially semi-circular in cross-section, extending distally therefrom. Angled wall 46 of proximal region 40 is positioned at an angle to the wall 45 of region 44, and illustratively at an obtuse angle. Wall 45 extends substantially parallel to a longitudinal axis of the delivery instrument. A first channel 48 has a first portion 48a extending longitudinally within region 44 (substantially parallel to the longitudinal axis) and an angled portion 48b extending along angled wall 46 transverse to the longitudinal axis of region 44. A second channel 50, substantially parallel to first channel 48, extends along regions 42 and 44. Channel 50 has a first portion 50a extending within region 44 and an angled portion 50b extending along angled wall 46 transverse to the longitudinal axis of region 44. Channels 48 and 50 terminate in distal openings 49, 51, respectively.

A cutting blade 60 is attached to channel housing 40 by pins 62, although other ways of attachment are also contemplated. As shown, blade 60 has a substantially planar surface 64 with an angled cutting edge 66 at a proximal edge.

Inner assembly 70 extends within housing 12 and tubular portion 14 and includes a threaded housing 72 and cap 80 as shown in FIG. 2. Threads 75 of housing 72 threadingly engage inner threads of cap 80. In certain embodiments, cap 80 is not provided, i.e. housing 72 is seated and secured in housing 12 without the cap 80. Inner shaft 74 extends distally from housing 72 within tube 14, preferably terminating at a distal end adjacent the distal end of the shaft 14. Spring 77 biases the assembly 70 in a proximal direction to hold and maintain the sutures 120, 122 taut.

The use of the delivery device 10 to deliver hole closure device 100 will now be described. In the initial position, the retainers 110 and 112 are positioned within inner shaft 74 which is received within elongated tube 14. Covering member 104 in this embodiment extends outside of the shaft 74 and tube 14 in the initial position and is maintained in a tilted delivery position by the delivery sheath through which delivery device 10 is inserted. However, it should be appreciated that in some embodiments, the covering member 104 can also be positioned in the shaft 74 or tube 14. In the initial position, projections 129 and 131 of sutures 120, 122, respectively, are out of engagement with the respective bumps on the bump housing 16 (see FIGS. 5 and 6).

Delivery device is inserted through a delivery sheath (not shown). In a preferred embodiment, device 10 is introduced through the delivery sheath such that the covering member 104, which extends outside the shaft 14, is placed inside the delivery sheath. To facilitate such insertion, a tube can be placed at the proximal end of the delivery sheath though which the covering member 104 is inserted.

The delivery device 10 is inserted through the delivery sheath, extending through the skin, the tissue puncture tract extending to the vessel wall, and through the vessel wall into the vessel lumen. In this position, deployment of the closure device 100 can now be initiated.

To deploy the closure device 100, the delivery device 10 is moved distally with respect to the delivery sheath to free the covering member 104 from the confines of the delivery sheath. Once exposed, the covering member 104 pivots within the vessel lumen from a first delivery position more aligned with the longitudinal axis of the delivery sheath to a transverse placement position.

The delivery device 10 is then retracted proximally to place the covering member 104 against the internal side of the opening in the vessel wall to patch or cover the vessel wall opening to prevent egress of fluid. Further proximal movement of the delivery device will then deploy the retainers 110, 112 to secure the hole closure device as described below. FIGS. 3, 5 and 6 show the initial position of the sutures 122 and 120 when the covering member 104 is initially inserted into the vessel lumen.

When the delivery device is retracted such that the covering member 104 abuts the internal vessel wall as mentioned above, further retraction of the delivery device will deploy the retainers 110, 112 as follows. In initial movement, suture 122 is pulled proximally such that engagement member 131 of suture 122 is moved into abutment/engagement with bump 32 as shown in FIGS. 7 and 7A. (Note the force of covering member 104 against the vessel wall provides a counterforce such that proximal movement of the delivery device and sutures 120, 122 cause distal movement of the retainers 110, 112 attached to the sutures 122, 120). The pulling (tensioning) of the suture 122 causes retainer 110, attached to the opposing end of suture 122, to move toward the covering member 104 as shown in FIG. 7. Note that the engagement member 129 of suture 120 is not yet engaged with bump 34 of bump housing 30. Thus, in this position, bump 32 provides a stop to restrict movement of the suture 122. This bump 32 also provides a tactile feel to the user to indicate that retainer 110 has moved a substantial distance toward covering member 104.

When delivery device 10 is pulled further proximally with respect to the delivery sheath it pulls (tensions) suture 120 proximally to move retainer 112 toward covering member 104 as shown in FIGS. 8 and 8A. Such movement continues until engagement member 129 abuts/engages bump 34. Bump 34 thereby provides a stop to limit movement of the suture 120. Bump 34 also provides a tactile feel to the user to indicate that retainer 112 has moved a substantial distance toward covering member 104. Note that engagement member 131 has already overcome bump 32 and is no longer in tension. As can be appreciated, retainers 110 and 112 have now been moved adjacent the covering member 104 but not yet in their fully distal securement position. Note this delivery method distributes the force, e.g. reduces the load on the covering member 104.

Continued proximal movement of delivery device 10 applies sufficient tension on suture 120 so engagement member 129 overrides bump 34 and continues its travel through longitudinal opening 20 and into longitudinal opening 22 until it engages bump 38 of longitudinal opening 22 as shown in FIG. 9 and FIG. 9A. This moves retainer 112 further distally toward covering member 104 to tighten retainer 112 with respect to covering member 104. Note engagement member 131 continues toward bump 36.

Continued proximal movement as shown in FIG. 10 pulls suture 122 proximally, out of longitudinal opening 24 and into longitudinal opening 26, until engagement member 131 engages bump 36. Projection 129 has overcome engagement with bump 34. Further movement of suture 122 moves retainer 110 further distally toward covering member 14, thereby tightening retainer 110 with respect to covering member 104, securing the covering member 104 in position. Note the extent of movement of the retainers 110, 112 toward the covering member 104, i.e. the final distance between the retainers 110 and 112 and between the retainers 110, 112 and covering member 104, will depend on the thickness of the patient's tissue.

With placement of the retainers 110 and 112 within the tissue tract leading to the vessel opening (but outside the vessel opening), the sutures 122, 124 are now severed automatically by the cutting blade 60 of delivery device 10. This is illustrated in FIGS. 11-13.

As the delivery device 10 is pulled further proximally, engagement members 129, 131 and sutures 120, 122 exit from openings 22, 26, respectively, of housing 16 and enter channels 48 and 50 of channel housing 40. As delivery device 10 is retracted and sutures 120 and 122 are retracted, engagement members 129, 131 drop within longitudinal portions 48a and 50a, with the sutures 120,122 remaining above these portions 48a, 48b to contact edge 66 of cutting blade 60 to sever the sutures 120, 122 as shown in FIG. 13. Note engagement members 129, 131 can float inside the channel because they are no longer in tension. The sutures 120, 122 can be further tightened and then trimmed by the surgeon to be flush with the patient's skin.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. In combination a vascular hole closure device and a delivery instrument for delivering the vascular hole closure device to a target site, the combination comprising:
   a vascular hole closure device having a covering member at a distal end for positioning internal of a vessel, a first retainer for positioning external of the vessel, a first flexible member extending between the covering member and first retainer and a first engagement member at a proximal portion of the flexible member; and
   a delivery instrument including a housing having a first stop, the first engagement member engageable with the first stop and overriding the first stop when a predetermined proximal force is applied to the delivery instrument, wherein proximal movement of the delivery instrument in a direction away from the covering member advances the first retainer toward the covering member, wherein the housing of the delivery instrument includes a lumen in which the first engagement member travels during delivery, and the first stop comprises an abutment member in the form of a projecting surface extending transversely of the lumen, wherein the delivery instrument includes a cutting member to sever the first flexible member upon delivery of the closure device to a surgical site.

2. The combination of claim 1, wherein in the initial position the first engagement member is spaced from the first stop and upon sufficient proximal movement of the delivery instrument the first engagement member engages the first stop.

3. The combination of claim 1, wherein the closure device comprises a second retainer for positioning external of the vessel, a second flexible member extending between the second retainer and covering member and a second engagement member at a proximal portion of the second flexible member, and the delivery instrument includes a second stop, the second engagement member engageable with the second stop and overriding the second stop when a predetermined proximal force in a direction away from the covering member is applied to the delivery instrument.

4. The combination of claim 3, wherein pulling of the first flexible member in a proximal direction advances the first retainer toward the covering member and pulling of the second flexible member in the proximal direction advances the second retainer toward the covering member, the proximal direction being the direction away from the covering member.

5. The combination of claim 4, wherein the covering member has first and second openings configured to restrict movement of the respective first and second flexible members.

6. The combination of claim 5, wherein the first and second openings of the covering member frictionally engage the respective first and second flexible members, and upon application of a sufficient force, the first and second flexible members can be moved through the first and second openings.

7. The combination of claim 4, wherein the covering member, first and second retainers and first and second flexible members are composed of a resorbable material.

8. The combination of claim 3, wherein the first and second retainers are placed in side by side relationship external of the vessel.

9. The combination of claim 3, wherein initial proximal movement of the delivery instrument moves the first retainer toward the covering member and subsequent proximal movement of the delivery instrument moves the second retainer toward the covering member.

10. The combination of claim 1, wherein the first retainer is fixedly secured to the first flexible member.

11. The combination of claim 1, wherein the delivery instrument has a first and second lumen, the first flexible member extends through the first and second lumen.

12. The combination of claim 1, wherein the delivery instrument has a first lumen to receive the first flexible member and the first stop reduces the cross-sectional dimension of the first lumen to provide resistance to movement of the first flexible member.

13. The combination of claim 1, wherein the delivery instrument includes an angled channel and a cutting member to sever the first flexible member within the angled channel.

14. In combination a vascular hole closure device and a delivery instrument for delivering the vascular hole closure device, the combination comprising:
   a vascular hole closure device having a covering member at a distal end for positioning internal of a vessel, a first retainer for positioning external of the vessel, a first flexible member extending between the covering member and first retainer and a first engagement member extending from the first flexible member; and a delivery instrument including a housing having a first lumen, the first flexible member movable within the first lumen when the delivery instrument is moved in a direction away from the covering member, a reduced cross sectional dimension area of the lumen engageable by the first engagement member to restrict movement of the first flexible member, wherein when a sufficient force is applied to the first engagement member, the first engagement member passes through the reduced cross-sectional dimension area so the first retainer is advanced toward the covering member, wherein the housing of the delivery instrument includes a third lumen in which the first engagement member travels during delivery, the first flexible member has a looped portion so it extends through the first and third lumens.

15. The combination of claim 14, wherein the closure device comprises a second retainer for positioning external of the vessel, a second flexible member extending between the second retainer and covering member and a second engagement member extending from the second flexible member, and the housing includes a second lumen, the second flexible member movable within the second lumen when the delivery instrument is moved in a direction away from the covering member, a reduced cross sectional dimension area of the lumen engageable by the second engagement member to restrict movement of the second flexible member, wherein when a sufficient force is applied to the second engagement member, the second engagement member passes through the reduced cross-sectional dimension area of the second lumen so the second retainer is advanced toward the covering member.

16. The combination of claim 15, wherein the covering member has first and second openings configured to restrict movement of the respective first and second flexible members.

17. In combination a vascular hole closure device and a delivery instrument for delivering the vascular hole closure device, the combination comprising:

a vascular hole closure device having a covering member at a distal end for positioning internal of a vessel, a first retainer for positioning external of the vessel, a first flexible member extending between the covering member and first retainer and a first engagement member extending from the first flexible member; and a delivery instrument including a housing having a first lumen, the first flexible member movable within the first lumen when the delivery instrument is moved in a direction away from the covering member, a reduced cross sectional dimension area of the lumen engageable by the first engagement member to restrict movement of the first flexible member, wherein when a sufficient force is applied to the first engagement member, the first engagement member passes through the reduced cross-sectional dimension area so the first retainer is advanced toward the covering member, wherein the delivery instrument includes a cutting member to sever the first flexible member.

* * * * *